United States Patent [19]

Orcutt

[11] 4,264,588
[45] Apr. 28, 1981

[54] **VACCINE FOR *CLOSTRIDIUM PERFRINGENS* TYPE E ENTEROTOXEMIA OF RABBITS**

[75] Inventor: Roger P. Orcutt, North Andover, Mass.

[73] Assignee: The Charles River Breeding Laboratories, Inc., Wilmington, Mass.

[21] Appl. No.: 37,734

[22] Filed: May 10, 1979

[51] Int. Cl.³ .............................................. A61K 39/08
[52] U.S. Cl. ...................................................... 424/92
[58] Field of Search .......................................... 424/92

[56] References Cited

U.S. PATENT DOCUMENTS

| | | | |
|---|---|---|---|
| 2,719,102 | 9/1955 | Baldwin | 424/92 |
| 3,099,601 | 7/1963 | Davis et al. | 424/92 |
| 3,288,680 | 11/1966 | Sterne | 424/92 |
| 3,579,633 | 5/1971 | Thomson | 424/92 |
| 3,983,229 | 9/1976 | Relyveld | 424/92 |
| 4,007,265 | 2/1977 | Holting | 424/92 |
| 4,029,765 | 6/1977 | Holting | 424/92 |

FOREIGN PATENT DOCUMENTS

| | | | |
|---|---|---|---|
| 895073 | 5/1962 | United Kingdom | 424/92 |
| 898783 | 6/1962 | United Kingdom | 424/92 |
| 901433 | 7/1962 | United Kingdom | 424/92 |
| 947912 | 1/1964 | United Kingdom | 424/92 |
| 958574 | 5/1964 | United Kingdom | 424/92 |
| 958575 | 5/1964 | United Kingdom | 424/92 |

OTHER PUBLICATIONS

Hauschild, A. H. W. *Clostridium-perfringens* Toxins Types B C D+E Microbial Toxins vol. IIa Bacterial Protein Toxins XIXAcad. Press NαYα1971:159–188.
Marasanova, L. P. ZhMikrobiol Epidemiol Immunobio 148 (8) 1971:116–121 Role of *Clostridium-perfringens* Types A B C D E+F in the Etiology of Gas Gangrene.
Sharmaeva, S. A. et al. ZhMikrobiol Epidemiol Immunobio 148 (8):58–63 1971, Study of Soluble *Clostridium-perfringens* Antigens Types D+E on Tissue Culture.
Zemlyanitskaya, E. P. et al. ZhMikrobiol Epidemiol Immunobio 146 (=):57–60 (1969), Effect of Proteolytic Enzymes on the Activity of Proto Toxins *Clostridium perfringens* Types D+E.
U2 Ermakova et al CαAα84:55085w (1976) Morphological Changes in the Cultures of Various Tissues Caused by *Clostridium perfringens* Toxins type B C D E+F.
Zemlyanitskaya E. P. et al. ZhMikrobiol Epidemiol Immunobio 146 (9):102–105 (1969) Study of Toxin Formation in *Clostridium perfringens* Type D+E in Dynamics.
Orcutt, R. P. et al. (1978) *Clostridium perfringens* Type E Enterotoxemia as a cause of acute diarrheal death or "hemorrhagic typlitis" in rabbits Abtract 100 Publication 78-4 Amer. Assoc. Lab Anim. Sci.
Patton, N. M. et al.(1978) Enterotoxemia in Rabbits Lab Anim. Sci. 28:536–540.
Katsaras K Effect of Trypsin and the Method of Injection of the Immunogenic Action of Toxins of *Clostridium perfringens* Types D+E Vet. Bull. 45 (8) 4238 1975.
McDonel, J. L. et al. Histopathological Effect of *Clostridium perfringens* Enterotoxin in the Rabbit Ileum Vet. Bull. 46 (4) 1804 (1976).

*Primary Examiner*—Shep K. Rose
*Attorney, Agent, or Firm*—Morse, Altman, Oates & Dacey

[57] ABSTRACT

A vaccine for *Clostridium perfringins* type E enterotoxemia of rabbits is produced by harvesting (or centrifuging) an actively growing culture of the bacterium and subjecting the supernatant to a proteolytic enzyme to produce a proteinaceous toxin characterized by a molecular weight of from 70,000 to 80,000 daltons, and inactivating the toxin by addition of a fixing agent to produce the toxoid along with any other toxins that might be present.

17 Claims, No Drawings

VACCINE FOR *CLOSTRIDIUM PERFRINGENS* TYPE E ENTEROTOXEMIA OF RABBITS

BACKGROUND OF THE INVENTION

1. Field of the Invention

The present invention relates to a toxoid(s) for the prevention of *Clostridium perfringins* type E enterotoxemia in rabbits and to a process for the production of this toxoid(s).

2. The Prior Art

Enteritides resulting in acute diarrhea are unquestionably the most serious causes of post weanling rabbit deaths in rabbitries surveyed throughout the world (Whitney, J. C. 1976, A Review of Non-Specific Enteritis in the Rabbit, Lab. Anim. 10: 209–221; Whitney, J. C., D. K. Blackmore, G. H. Townsend, R. J. Parkin, M. E. Hugh-Jones, P. J. Crossman, T. Graham-Marr, A. C. Rowland, M. F. W. Festing and D. Krzysiak, 1976, Rabbit Mortality Survey, Lab. Anim. 10: 203–207). Unfortunately, aside from diarrheas of known causes such as salmonellosis and coccidiosis, controversy still exists as to the classification and the etiology of various other types of rabbit entertides (Flatt, R. E. 1974, Bacterial Diseases, Pg. 194–236, In, S. H. Weisbroth, R. E. Flatt and A. L. Kraus (Ed.), The Biology of the Laboratory Rabbit, Academic Press, Inc., New York; Meshorer, A. 1976, Histological Findings in Rabbits Which Died of Mucoid Enteritis, Lab. Anim. 10: 199–202; Whitney, J. C. 1976, a Review of Non-Specific Enteritis in the Rabbit, supra). Nevertheless, one major cause of acute diarrheal death in rabbits has long been recognized as an enterotoxemia (Lesbouyries, G. and M. Berthelon, 1936, Enterotoxemia du lapin, Bull. Acad. Vet. Fr. 9: 74–82) and, until recently, the etiological agent had not been identified (Orcutt, R. P., H. L. Foster and A. M. Jonas, 1978, *Clostridium perfringens* type E Enterotoxemia as a Cause of Acute Diarrheal Death or "Hemorrhagic Typhlitis" in Rabbits, Absrt. #100 in Publication 78-4 of the Amer. Assoc. Lab. Anim. Sci.; Patton, N. M., H. T. Holmes, R. J. Riggs, and P. R. Cheeke, 1978, Enterotoxemia in Rabbits, Lab. Anim. Sci. 28: 536–540).

BRIEF SUMMARY OF THE INVENTION

The object of the present invention is to provide a vaccine for *Clostridium perfringens* type E enterotoxemia of rabbits, said vaccine comprising an aqueous vehicle and a toxoid(s) characterized by at least one *Clostridium perfringens* type E protein having a molecular weight of from 70,000 to 80,000 daltons. Preferably, the vaccine is produced by the following steps. A culture of the bacterium is grown in either a cooked meat medium or a Duncan/Strong medium (Duncan, C. L. and D. H. Strong, 1968, Improved Medium For Sporulation of *Clostridium perfringens*, Appl. Micro. 16:82–89) for a periof of from 18 to 24 hours to produce an aqueous culture containing a heavy, approximately maximal, concentration of active *Clostridium perfringens* type E bacteria. A supernatant fluid is obtained by centrifuging the culture at 3,000–10,000 times gravity and decanting. To this supernatant liquid is added a proteolytic enzyme in the amount of 1.0 to 100 micrograms per milliliter, the supernatant fluid being at the active temperature of the enzyme, usually from 30° to 40° C. This temperature is maintained for a period of from 30 to 60 minutes to produce a proteinaceous toxin having a molecular weight generally in the range of from 70,000 to 80,000 daltons. In the case of the cooked meat medium, the supernatant is either not dialyzed or is dialyzed at a molecular weight cut-off of from 10,000 to 70,000 daltons. In the case of the Duncan/Strong medium, the supernatant is not dialyzed. In all cases, the pH is maintained at from 5 to 9. Then a fixing agent, is added to the supernatant in the amount of 0.01% to 5.0%. The resulting clear aqueous solution of dissolved inactivated bacterial protein (and other bacterial residue) finally is incubated at a temperature ranging from 4° to 40° C. for a period ranging from 1 hour to 14 days and thereafter the resulting toxoid is stored at a temperature ranging from 1° to 30° C. In an alternative embodiment, an adjuvant (e.g. alum) is added to the aforementioned toxoid in an amount ranging from 0.5 to 20% by total weight. In another alternative embodiment, a sub-lethal concentration of active toxin is added to the aforementioned toxoid. It has been found that the toxoid of the present invention is concentrated and potent.

DETAILED EXAMPLE OF THE MATERIALS AND METHODS OF THE PREFERRED EMBODIMENT

The rabbits utilized herein were of the type sold by The Charles River Breeding Laboratories, Inc. under the trade designation COBS (NZW) BR strain initiated in 1973 by associating an isolator colony of axenic rabbits with isolates of autochthonous rabbit intestinal bacteria (Orcutt, R. P. 1976, The Chronological Colonization of the Intestine of The Conventional Rabbit by the Normal Gut Microflora, Absrt. #36 in Publication 76-2 of Amer. Assoc. Lab. Anim. Sci.). The mice used for titering the toxin were five-week old males, sold by The Charles River Breeding Laboratories under the trade designation CD-1 (ICR) BR.

Toxin Production

Primarily iota toxin, but undoubtedly other toxins of *Clostridium perfringens* type E, were produced in vitro by the trypsinization of supernatant fluids of either cooked meat medium or Duncan/Strong medium (Duncan, C. L. and D. H. Strong, 1968, Improved Medium for Sporulation of *Clostridium perfringens*, supra).

Toxin was produced in cooked meat medium as follows. An 18-hour old colony of *Clostridium perfringens* type E was inoculated into 20 ml of cooked meat medium at 9:00 a.m. and allowed to incubate anaerobically at 35° C. until 4:00 p.m. of the same day. One milliliter of this actively growing culture then was transferred into one liter of the same medium and incubated at 35° C. until 8:00 a.m. the following morning. The culture then was placed in an ice bath for 30 minutes, was passed through cheesecloth to remove large pieces of cooked meat, was centrifuged at 8,000×1 normal gravity (g) for ten minutes at 10° C. and the supernatant finally was decanted. An aqueous solution of trypsin (Difco 1:250) was added to a concentration of 0.1 percent and the supernatant was incubated at 37° C. for 45 minutes, was passed through a 0.45 micron (millipore) filter and then was stored at 4° C. in sterile bottles until use. This preparation routinely produced 16–32 $LD_{50}$ (doses that are lethal with a probability of 50%) units/ml when titered in mice.

Toxin was produced in Duncan/Strong medium by inoculating one colony of *Clostridium perfringens* type E into 10 cc of thioglycollate broth and incubating it for 16–20 hours aerobically at 37° C. This entire 10 cc culture then was inoculated into 100 ml of Duncan/Strong medium and was incubated aerobically at 37° C. for three hours. The entire 110 ml culture then was inoculated into one liter of Duncan/Strong medium and incubated overnight at 37° C. aerobically. The following morning, the culture was placed in an ice bath for 30 minutes, centrifuged at 8,000× g for ten minutes at 10° C. and the supernatant was decanted. Purified trypsin (ICN) was then added to a final concentration of 10 micrograms per ml and the supernatant was incubated at 37° C. for 30 minutes. The trypsinized supernatant fluid then was aliquoted and refrigerated at 4° C. until use.

Toxin Quantitation

Serial two-fold dilutions of toxin were prepared in phosphate buffered saline (pH 7.3) and 0.5 cc quantities of each dilution were injected intraperitoneally into each of four mice with a 25 gauge needle. Mice were observed for mortality for three days and the titers were expressed as mouse $LD_{50}$ units/ml. Toxin preparations routinely titered between 16 and 32 mouse $LD_{50}$ units/ml. Trypsinized cooked meat medium supernatant was nontoxic when injected identically into mice.

Serum Neutralization Tests

Rabbits utilized in this study were shown to be free of antibody to the toxins of Clostridium perfrigens type E as follows. Blood was obtained by cardiac puncture and 0.4 ml of undiluted serum was mixed with 2.0 ml of toxin containing four mouse $LD_{50}$ units/ml and allowed to incubate at room temperature for 30 minutes. Each of four mice then was injected with 0.5 ml of the serum/toxin mixture. Mice were observed for three days and all rabbits were found to lack any neutralizing activity against the toxin. Clostridium perfringens type E antiserum (Burrough's Wellcome) was used in an identical manner as a positive control.

Toxoid Production

The toxin(s) was (were) attentuated to a toxoid(s) by adding formalin to a final concentration of 0.4 percent and incubating at room temperature for 1-2 weeks. The attenuation was considered to be complete when undiluted 0.5 cc aliquotes injected i.p. were no longer lethal to mice. The toxoid then was stored at 4° C. Uninoculated and trypsinized cooked meat medium supernatant containing 0.4 percent formalin was found to be nontoxic to mice when injected in an identical manner.

Vaccination Procedures

Female rabbits received three subcutaneous injections of 2.0 ml of toxoid spaced two weeks apart. A 20 gauge needle was used and the injection site was in the cervical region of the back.

Challenge Procedure

Rabbits were challenged by intravenous injection in the marginal ear vein of toxin containing 16 mouse $LD_{50}$ units/ml. Each rabbit received 1 ml of the toxin preparation per pound of body weight.

Results

Six vaccinated and three control rabbits were challenged two weeks after their last injection of toxoid. As indicated in Table 1 below, all six vaccinated rabbits remained completely asymptomatic while the three control rabbits died between three minutes and 2.25 hours. In order to determine the length of immunity conferred by the vaccination regimen, two groups of rabbits were vaccinated, one of which was challenged approximately six months and the other at nine months following the last injection. As indicated in Table 2 below, complete protection was noted with all five rabbits challenged 5.5 months post vaccination while only two of six rabbits survived the challenge dose when it was administered nine months post vaccination. Consequently, animals vaccinated with this toxoid prepared in cooked meat medium should receive a booster approximately every six months.

TABLE 1

Efficacy of Clostridium perfringens Type E Toxoid Prepared in Cooked Meat Medium

| Rabbit # | Treatment[a] | Serum Titers[b] Day 0 | 14 | Following Injection 28 | 43 | Challenge Results |
|---|---|---|---|---|---|---|
| 1 (7.1 lbs) | V | 0 | U | 0 | U | No Effect |
| 2 (7 lbs) | V | 0 | 0 | 0 | U | No Effect |
| 3 (8.4 lbs) | V | 0 | U | U | 4 | No Effect |
| 4 (6.3 lbs) | V | 0 | U | U | 2 | No Effect |
| 5 (6.8 lbs) | V | 0 | U | U | 2 | No Effect |
| 6 (6 lbs) | V | 0 | U | 0 | U | No Effect |
| 7 (7.6 lbs) | C | 0 | 0 | 0 | 0 | Died in 2 hrs. 15 min. |
| 8 (6.5 lbs) | C | 0 | 0 | 0 | 0 | Died in 10 minutes |
| 9 (7.3 lbs) | C | 0 | 0 | 0 | 0 | Died in 3 minutes |

[a] V = Vaccinated on Days 0, 14 and 28 C = Control rabbits injected with uninoculated cooked meat medium supernatant on Days 0, 14 and 28.
[b] U = Undiluted serum

TABLE 2

Length of Immunity Against the Toxins of Clostridium perfringens Type E Conferred On Rabbits by Toxoid

| Rabbit # | Treatment[a] | Weight (Lbs.) | Challenge Time[b] | Challenge Results |
|---|---|---|---|---|
| 1 | V | 5.0 | 5.5 | No Effect |
| 2 | V | 10.0 | 5.5 | No Effect |
| 3 | V | 10.0 | 5.5 | No Effect |
| 4 | V | 10.0 | 5.5 | No Effect |
| 5 | V | 12.0 | 5.5 | No Effect |
| 6 | C | 6.0 | 5.5 | Died |
| 7 | V | 5.3 | 9.0 | Died |
| 8 | V | 8.0 | 9.0 | No Effect |
| 9 | V | 8.5 | 9.0 | Died |
| 10 | V | 9.7 | 9.0 | Died |
| 11 | V | 10.3 | 9.0 | Died |
| 12 | V | 13.5 | 9.0 | No Effect |
| 13 | C | 5.0 | 9.0 | Died |
| 14 | C | 5.0 | 9.0 | Died |
| 15 | C | 11.5 | 9.0 | Died |

TABLE 2-continued

Length of Immunity Against the Toxins of
Clostridium perfringens Type E Conferred
On Rabbits by Toxoid

| Rabbit # | Treatment(a) | Weight (Lbs.) | Challenge Time(b) | Challenge Results |
|---|---|---|---|---|
| 16 | C | 11.5 | 9.0 | Died |

(a)V = Vaccinated, C = Unvaccinated control
(b)Time in months following vaccination when animals were challenged.

Since certain changes may be made in the present disclosure without departing from the invention involved, it is intended that all matter described in the foregoing specification be interpreted in an illustrative and not in a limiting sense.

What is claimed is:

1. A vaccine for *Clostridium perfringens* type E enterotoxemia of rabbits, said vaccine constituting a toxoid solution reaction product in an aqueous vehicle of a fixing agent and the toxins of *Clostridium perfringens* type E, at least one of which is a protein having a molecular weight in the approximate range of from 70,000 to 80,000 daltons, said aqueous vehicle containing the supernatant liquid harvested from an actively growing culture of primarily-iota-toxin producing *Clostridium perfringens* type E bacteria, said toxoid solution having a pH within the range of from 5 to 9, said fixing agent containing aldehyde as its essential ingredient and having a concentration within the approximate range of from 0.01% to 5.0% with respect to said supernatant liquid.

2. The vaccine of claim 1 wherein said aqueous vehicle includes the supernatant liquid of a cooked meat medium.

3. The vaccine of claim 1 wherein said aqueous vehicle includes the supernatant liquid of a Duncan/Strong medium.

4. The vaccine of claim 1 wherein said fixing agent is formalin.

5. A method for producing a vaccine for *Clostridium perfringens* type E enterotoxemia of rabbits, said method comprising the steps of growing a culture of primarily iota-toxin-producing *Clostridium perfringens* type E bacteria in a culture medium for a period necessary to produce an aqueous liquid containing an approximately maximal concentration of actively growing, primarily iota-toxin-producing *Clostridium perfringens* type E bacteria, adding to said liquid a proteolytic enzyme in an amount of from 1.0 to 100 micrograms per milliliter, said liquid being at the active temperature of said enzyme to produce a proteinaceous toxin liquid characterized by a proteinaceous toxin having a molecular weight in the range of from 70,000 to 80,000 daltons, adding to said proteinaceous toxin a fixing agent containing an aldehyde as its essential ingredient and having a concentration within the approximate range of 0.01 to 5.0% with respect to said liquid in order to provide a toxoid/bacterin combination and to kill said bacteria, maintaining said toxoid/bacterin combination at a pH ranging from 5 to 9, and incubating said toxoid/bacterin combination for a period ranging from 1 hour to 14 days at a temperature ranging from 4° to 40° C.

6. The method of claim 5 wherein said supernatant is that of a cooked meat medium.

7. The method of claim 5 wherein said supernatant is that of a Duncan/Strong medium.

8. The method of claim 5 wherein said proteolytic enzyme is trypsin.

9. The method of claim 5 wherein said fixing agent is formaldehyde.

10. The method of clain 5 wherein alum is added as an adjuvant in a concentration from 0.5% to 20% by total weight.

11. The method of claim 5 wherein the culture is not centrifuged so that all the bacteria from the growth are present along with the toxoid.

12. The method of claim 11 wherein alum is added as an adjuvant in a concentration of from 0.5% to 20% by total weight.

13. A vaccine for *Clostridium perfringens* type E enterotoxemia of rabbits, said vaccine constituting a toxoid/bacterin combination, in a liquid vehicle, comprising the reaction product of:

(a) growing a culture of primarily iota-toxin-producing *Clostridium perfringens* type E bacteria for a period ranging from 18 to 24 hours in a culture medium to produce an aqueous liquid containing an approximately maximal concentration of live primarily iota-toxin-producing *Clostridium perfringens* type E bacteria;

(b) adding to said supernatant liquid, while said culture is actively growing, the proteolytic enzyme trypsin in an amount of from 1.0 to 100 micrograms per milliliter;

(c) maintaining the resulting liquid at a temperature in the range of from 30° to 40° C. for a period in the range of from 30 to 60 minutes to produce a proteinaceous toxin liquid characterized by a proteinaceous toxin having a molecular weight in the range of from 70,000 to 80,000 daltons;

(d) adding to said proteinaceous toxin liquid a formaldehyde containing fixing agent to provide a formaldehyde concentration approximately in the range of from 0.01 to 5.0% in order to kill said bacteria and to produce a toxoid; and (e) incubating said toxoid at a pH in the range of from 5 to 9 for a period in the range of from 1 hour to 14 days at a temperature in the range of from 4° to 40° C.

14. The process of vaccinating rabbits with a vaccine for *Clostridium perfringens* type E enterotoxemia of rabbits, said vaccine constituting a toxoid solution reaction product in an aqueous vehicle of a fixing agent and a primarily iota-toxin-producing *Clostridium perfringens* type E protein having a molecular weight in the range of from 70,000 to 80,000 daltons, said aqueous vehicle containing the supernatant liquid from an actively growing culture of primarily iota-toxin-producing *Clostridium perfringens* type E bacteria, said toxoid solution having a pH within the range of from 5 to 9, said fixing agent containing an aldehyde as its essential ingredient and having a concentration within the approximate range of from 0.01% to 5.0% with respect to said supernatant liquid.

15. A method of vaccinating rabbits against *Clostridium perfringens* type E enterotoxemia, said method comprising the steps of growing a culture of primarily iota-toxin-producing *Clostridium perfringens* type E bacteria in a culture medium for a period necessary to produce an aqueous toxoid/bacterin combination containing an approximately maximal concentration of actively growing *Clostridium perfringens* type E bacteria and toxins, adding to said supernatant liquid a proteolytic enzyme in an amount of from 1.0 to 100 micrograms per milliliter, said supernatant liquid being at the active temperature of said enzyme to produce a proteinaceous toxin liquid characterized by toxins of *Clostridium perfringens* type E, at least one of which is the iota toxin having a molecular weight in the range of from 70,000 to 80,000 daltons, adding to said combination of fixing agent containing an aldehyde as its essential ingredient and having a concentration within the approximate range of 0.01 to 5.0% with respect to said toxoid/bacterin combination in order to provide a toxoid and to kill said bacteria, maintaining the product at a pH ranging from 5 to 9, incubating said product for a period ranging from 1 hour to 14 days at a temperature ranging from 4° to 40° C., and injecting each of said rabbits on three occasions spaced at two week intervals with approximately 2 ml. doses of said product in order to immunize said rabbits against said enterotoxemia.

16. The vaccine of claim 1, wherein the proteolytic enzyme is added to the supernatant liquid harvested from the aqueous vehicle.

17. The vaccine of claim 16, wherein said proteolytic enzyme is trypsin.

* * * * *